(12) United States Patent
Schleich

(10) Patent No.: US 9,067,068 B2
(45) Date of Patent: *Jun. 30, 2015

(54) CHANNEL SPECIFIC GAIN CONTROL INCLUDING LATERAL SUPPRESSION

(71) Applicant: MED-EL Elektromedizinische Geraete GmbH, Innsbruck (AT)

(72) Inventor: Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 109 days.

This patent is subject to a terminal disclaimer.

(21) Appl. No.: 13/767,036

(22) Filed: Feb. 14, 2013

(65) Prior Publication Data

US 2013/0158629 A1 Jun. 20, 2013

Related U.S. Application Data

(63) Continuation-in-part of application No. 12/695,240, filed on Jan. 28, 2010, now Pat. No. 8,412,343.

(60) Provisional application No. 61/147,855, filed on Jan. 28, 2009.

(51) Int. Cl.
*A61N 1/36* (2006.01)

(52) U.S. Cl.
CPC .................... *A61N 1/36032* (2013.01)

(58) Field of Classification Search
CPC .................... A61N 1/0541; A61N 1/36032
USPC .................................. 607/55, 56, 57
See application file for complete search history.

(56) References Cited

U.S. PATENT DOCUMENTS 7,242,985 B1 * 7/2007 Fridman et al. .............. 607/56
8,412,343 B2 * 4/2013 Schleich ...................... 607/57

* cited by examiner

*Primary Examiner* — Alyssa M Alter
(74) *Attorney, Agent, or Firm* — Sunstein Kann Murphy & Timbers LLP

(57) ABSTRACT

A system is described for generating electrode stimulation signals for stimulation electrodes in an implanted electrode array on a given side of a bilateral cochlear implant system. A pre-processor module processes an acoustic audio signal with a bank of filters to generate a set of band pass signals each corresponding to a band of audio frequencies associated with one of the filters. An automatic gain control (AGC) circuit performs a channel specific dynamic amplitude mapping of the band pass signals to generate a set of compressed band pass signals. The AGC circuit uses a bilateral multiplication matrix characterizing a lateral suppression network and having at least one non-zero coupling element from a contralateral side. A stimulation timing module extracts stimulation information from the compressed band pass signals to generate stimulation timing signals. A pulse shaper module develops the stimulation timing signals into electrode stimulation signals to the stimulation electrodes.

20 Claims, 7 Drawing Sheets

9,067,068 B2

CHANNEL SPECIFIC GAIN CONTROL INCLUDING LATERAL SUPPRESSION

This application is a continuation-in-part of U.S. patent application Ser. No. 12/695,240, filed Jan. 28, 2010, which in turn claims priority from U.S. Provisional Application 61/147,855, filed Jan. 28, 2009; all of which are incorporated herein by reference.

FIELD OF THE INVENTION

The present invention relates to medical implants, and more specifically to signal processing for cochlear implant systems.

BACKGROUND ART

In a cochlear implant (CI) the amplitude of the acoustic audio signal has to be mapped to a relatively small dynamic range which can be delivered to the acoustic nerve. Typically two stages perform this amplitude compression, a front-end automatic gain control (AGC) which controls the overall loudness and an instantaneous non-linear mapping function of typically logarithmic shape which further compresses each band-pass envelope. The dynamic AGC used in current CI systems usually applies one gain to the entire analyzed frequency range before splitting the acoustic audio signal into individual frequency bands. Such systems have been shown to increase listening comfort and speech understanding in hearing aid (HA) users as well as CI users.

One possible drawback of such a system can occur in the presence of two signals which are located in different frequency regions, such as a speech signal in the presence of a continuous high frequency noise. In such an acoustic environment, the AGC gain would depend on the relative amplitudes of the two signals. Assuming a loud high frequency noise, the AGC gain would be reduced by the noise signal which could result in suppression of the speech signal. In a unilaterally implanted patient, this might only result in reduced speech understanding. But in bilaterally implanted patients, there could also be a reduced ability to localize sound sources. For example, assuming the loud high frequency noise source is located at the right side of the CI user, then the right-side AGC would reduce its gain more than the left-side AGC. Consequently, the interaural level differences at high frequencies would be reduced, and since the acoustic head shadow effect is higher at high frequencies, the interaural level difference at low frequency could vanish or even be inverted. As a result, the low frequency components, for example originating from a car engine, would be perceived from the wrong side.

These undesirable side effects of front-end single channel signal compression could generally be circumvented by using AGCs which compress individual band pass signals instead of the broadband signal. Such solutions can be found both in hearing aids and in cochlear implant systems. Speech understanding in the presence of noise sounds and sound localization in bilateral patients could potentially be enhanced. One major drawback of such systems is the fact that spectral differences such as amplitude differences in adjacent analysis bands get reduced. Spectral information such as formant frequencies in speech signals could also be less accessible to HA and CI users.

There have been previous efforts to apply dynamic compression to band pass signals. For example, FIG. 1 shows an arrangement described in U.S. Pat. No. 7,136,706 (incorporated herein by reference) which applies an overall mapping to a pre-band pass signal and then band specific mapping. The pre-band pass mapping function is thought to be linear (i.e. a limiter). The post-band pass mapping function is implemented as a non-linear, compressive, or logarithmic transform. The inventors state that the differences in acoustic spectrum component amplitudes are maintained. By maintaining these differences, spectral smearing between channels is reduced and speech cues are preserved. But dynamic adaptation of post-band pass compression would result in unwanted spectral smearing.

A second method which applies frequency specific gains is described in U.S. Pat. No. 6,731,767 (incorporated herein by reference). As shown in the block diagram in FIG. 2, an acoustic audio signal is split into a number of separate frequency bands and variable gain is applied to each frequency band independently. In contrast to previously used AGC circuits, the gain is controlled by a gain comparator and statistical estimates of each band pass signal are calculated and compared to predetermined hearing response parameters. Although the gain calculation appears to be dynamic in this patent, it does not describe any interaction between analysis channels.

U.S. Pat. No. 7,305,100 describes a dynamic compression process which applies channel specific gains for use in a hearing aid, although no mention is found of use in a cochlear implant system. Although as shown in FIG. 3, there is a gain control unit, no details are discussed with regards to interactions between the analysis frequency bands.

U.S. Patent Publication 2004/0136545 describes an arrangement for distributed gain control which takes into account the interactions between analysis channels. FIG. 4 shows a block diagram of the arrangement discussed which is described as providing a spectral enhancement system that includes distributed filters, energy distribution units, and a weighted-averaging unit. Instead of filter banks as used in cochlear implants and hearing aids, a filter cascade is used with an energy-detector that is coupled to each filter and provides an energy-detection output signal. A weighted-averaging unit provides a weighted-averaging signal to each of the filters and distributed gain is applied to the filter stages via a nonlinear function.

SUMMARY OF THE INVENTION

Embodiments of the present invention are directed to a system and method for generating electrode stimulation signals for stimulation electrodes in an implanted electrode array on a given side of a bilateral cochlear implant system. A pre-processor module processes an acoustic audio signal with a bank of filters to generate a set of band pass signals each corresponding to a band of audio frequencies associated with one of the filters. An automatic gain control (AGC) circuit performs a channel specific dynamic amplitude mapping of the band pass signals to generate a set of compressed band pass signals. The AGC circuit uses a bilateral multiplication matrix characterizing a lateral suppression network and having at least one non-zero coupling element from a contralateral side. A stimulation timing module extracts stimulation information from the compressed band pass signals to generate stimulation timing signals. A pulse shaper module develops the stimulation timing signals into electrode stimulation signals to the stimulation electrodes.

The AGC circuit may include a delay circuit that delays the amplitude mapping of the band pass signals by one or more samples and/or that downsamples the multiplication matrix. A gain calculation circuit may apply an individual gain constant, which may be the same for all band pass signals, or different for different band pass signals. The gain calculation circuit may include an inverting functionality. A level compressor may perform a non-linear mapping of the lateral suppression network, for example using a non-linear MAP-law. The lateral suppression network may include interaural level differences.

DETAILED DESCRIPTION OF SPECIFIC EMBODIMENTS

Various embodiments of the present invention are directed to extending cochlear implant signal processing with an additional signal processing block that calculates channel specific dynamic amplitude mapping with gain suppression. Such an approach can enhance spectral details and model masking effects as known from normal hearing psychoacoustics. In addition, channel specific interaural level differences can be preserved in patients with bilateral cochlear implants.

Figure 1:
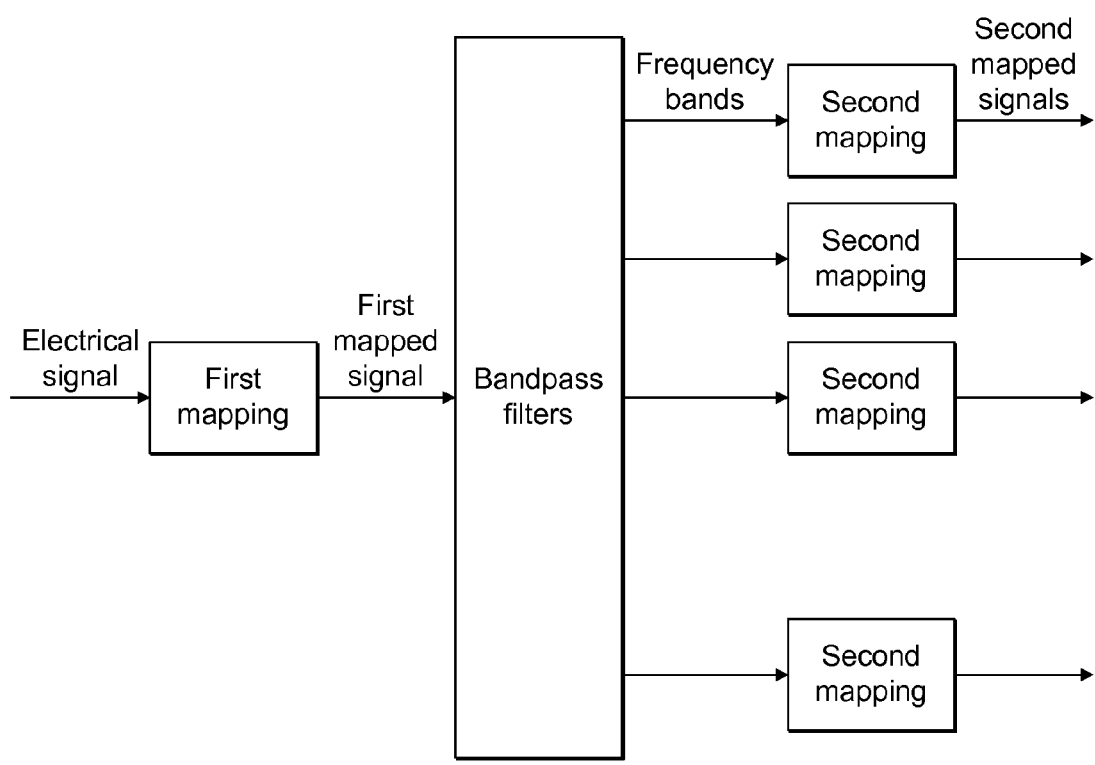
FIG. 1 shows a typical prior art cochlear implant signal compression arrangement.
Figure 2:
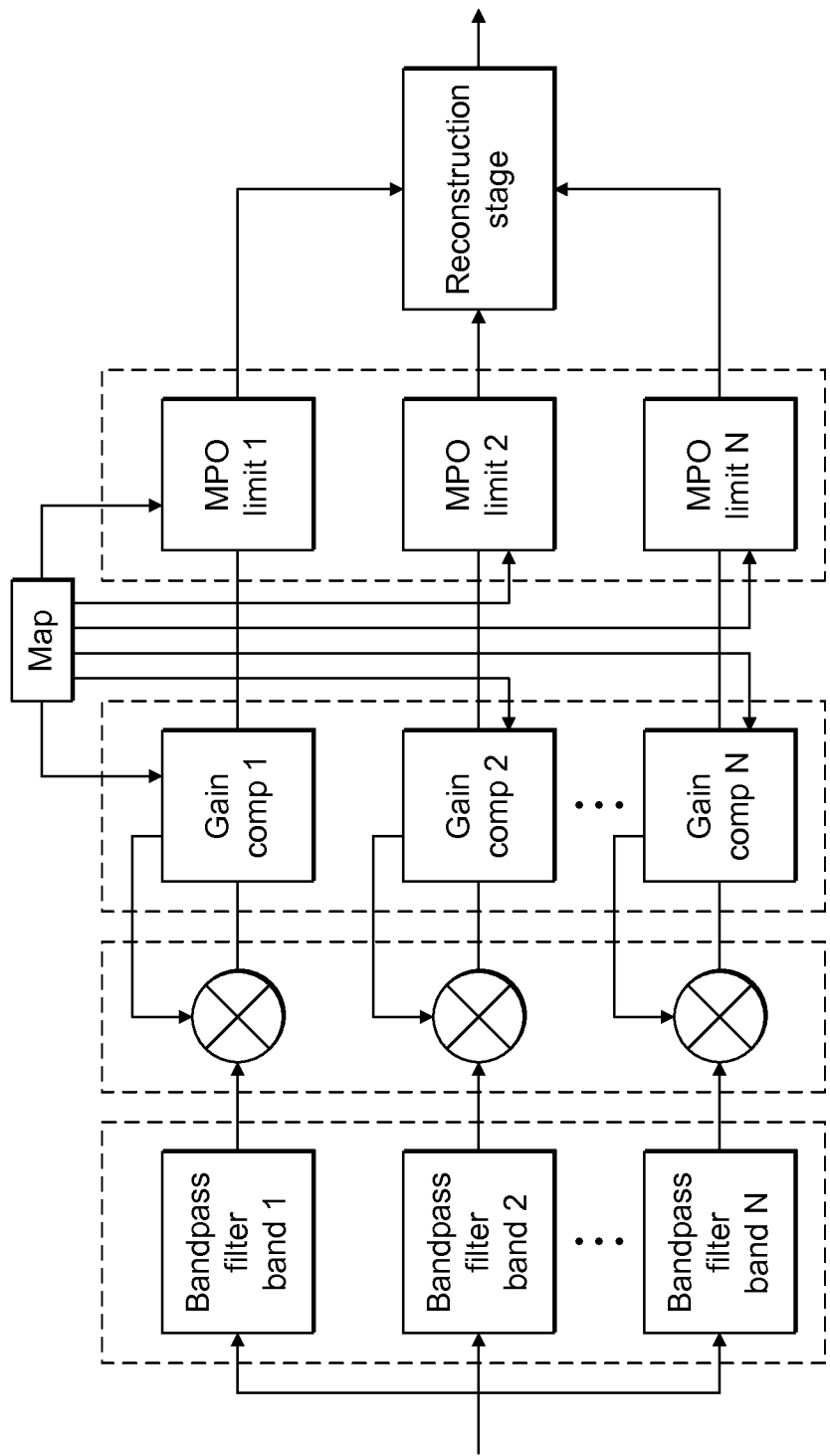
FIG. 2 shows a prior art signal compression arrangement having independent channels.
Figure 3:
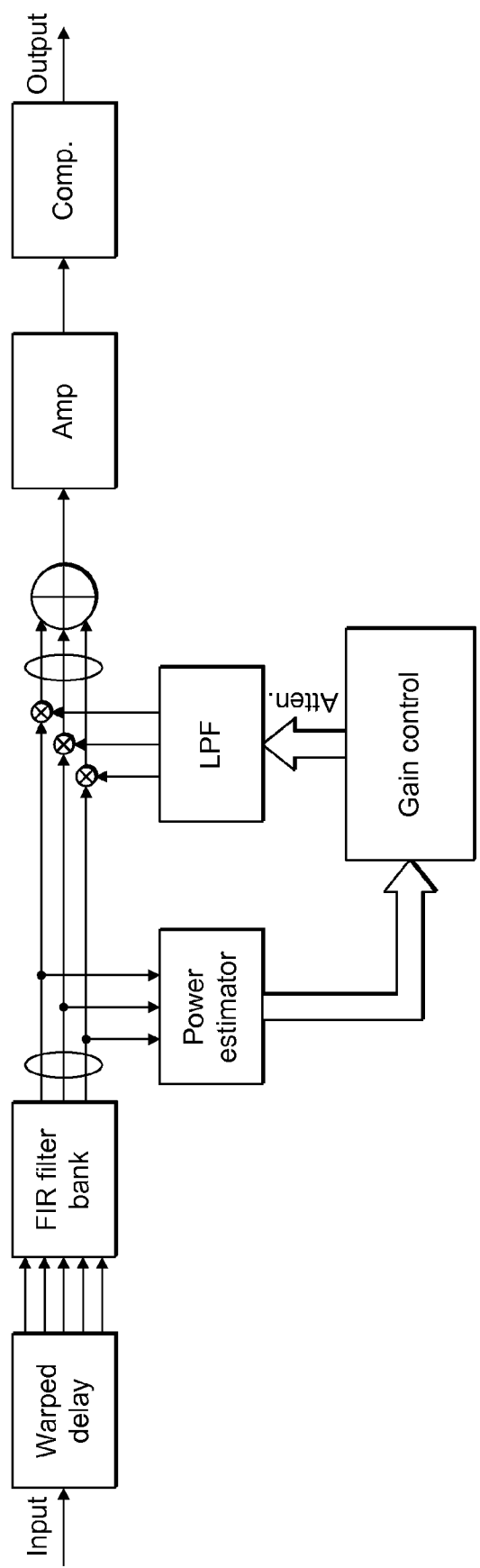
FIG. 3 shows a prior art signal compression arrangement having non-interactive channel specific gains.
Figure 4:
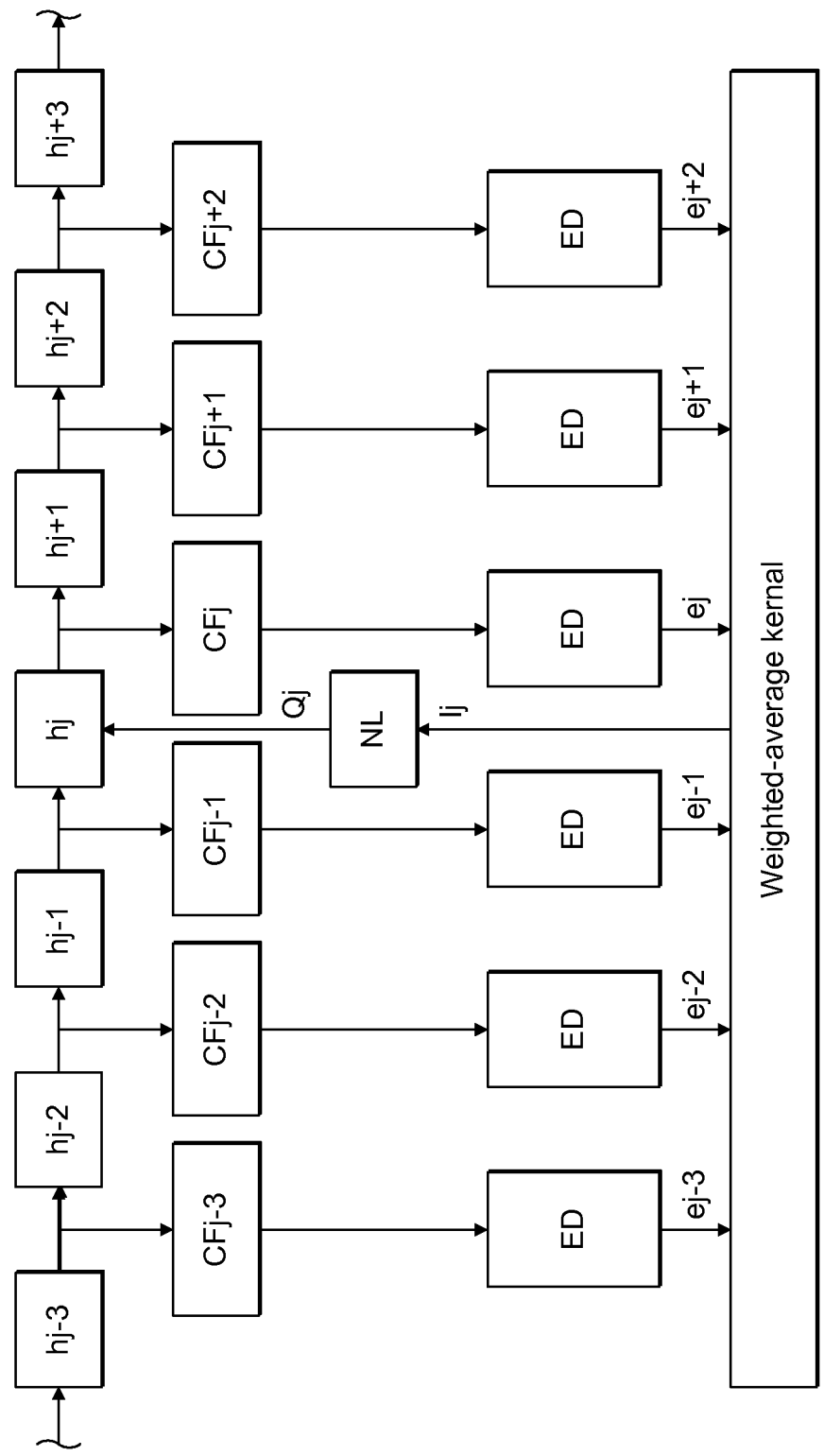
FIG. 4 shows a prior art signal compression system based on a filter cascade arrangement.
Figure 5:
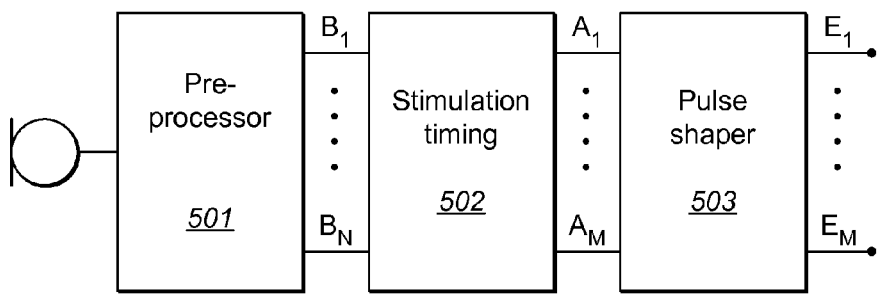
FIG. 5 shows a block diagram of a typical cochlear implant signal processing arrangement.

FIG. 5 shows various function blocks in a typical cochlear implant signal processing arrangement for generating electrode stimulation signals for the stimulation electrodes in an implanted electrode array. A pre-processor module 501 initially pre-processes an acoustic audio signal from a sensing microphone (e.g., by an initial AGC, a limiter, and/or noise reduction means) and then uses a filter bank to split the audio signal into a set of band pass signals $B_n$ where each band pass signal corresponds to a band of audio frequencies associated with one of the filters. A stimulation timing module 502 performs information extraction and decimation to derive or determine a set of stimulation timing signals $A_m$ which in effect maps the filter analysis frequency bands to the stimulation electrodes. From these, a pulse shaper module 503 performs an amplitude mapping and pulse shape definition to define a set of stimulation pulses $E_m$ for the stimulation electrodes.

Figure 6:
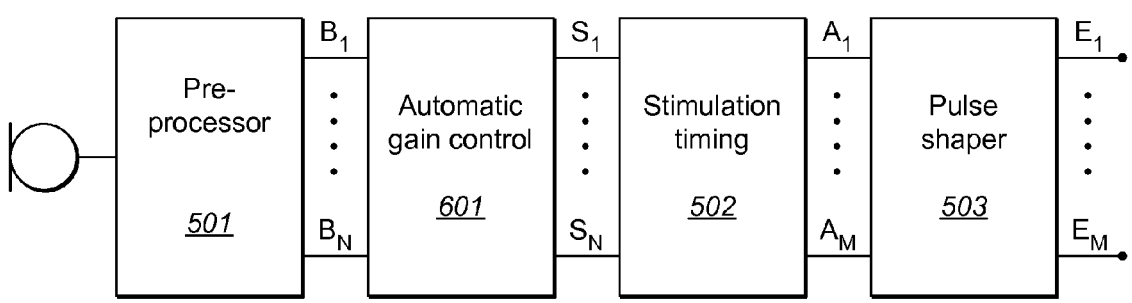
FIG. 6 shows a block diagram for a cochlear implant signal processing arrangement including channel specific volume control according to an embodiment of the present invention.

FIG. 6 shows functional blocks according to an embodiment of the present invention where an automatic gain control (AGC) module 601 uses a lateral suppression network to perform channel specific dynamic amplitude mapping of the band pass signals to generate a set of compressed band pass signals $S_n$ from the pre-processor module 501. The stimulation timing module 502 then derives the stimulation timing signals $A_m$ from the compressed band pass signals $S_n$ and the pulse shaper module 503 produces the stimulation pulses $E_m$.

Figure 7:
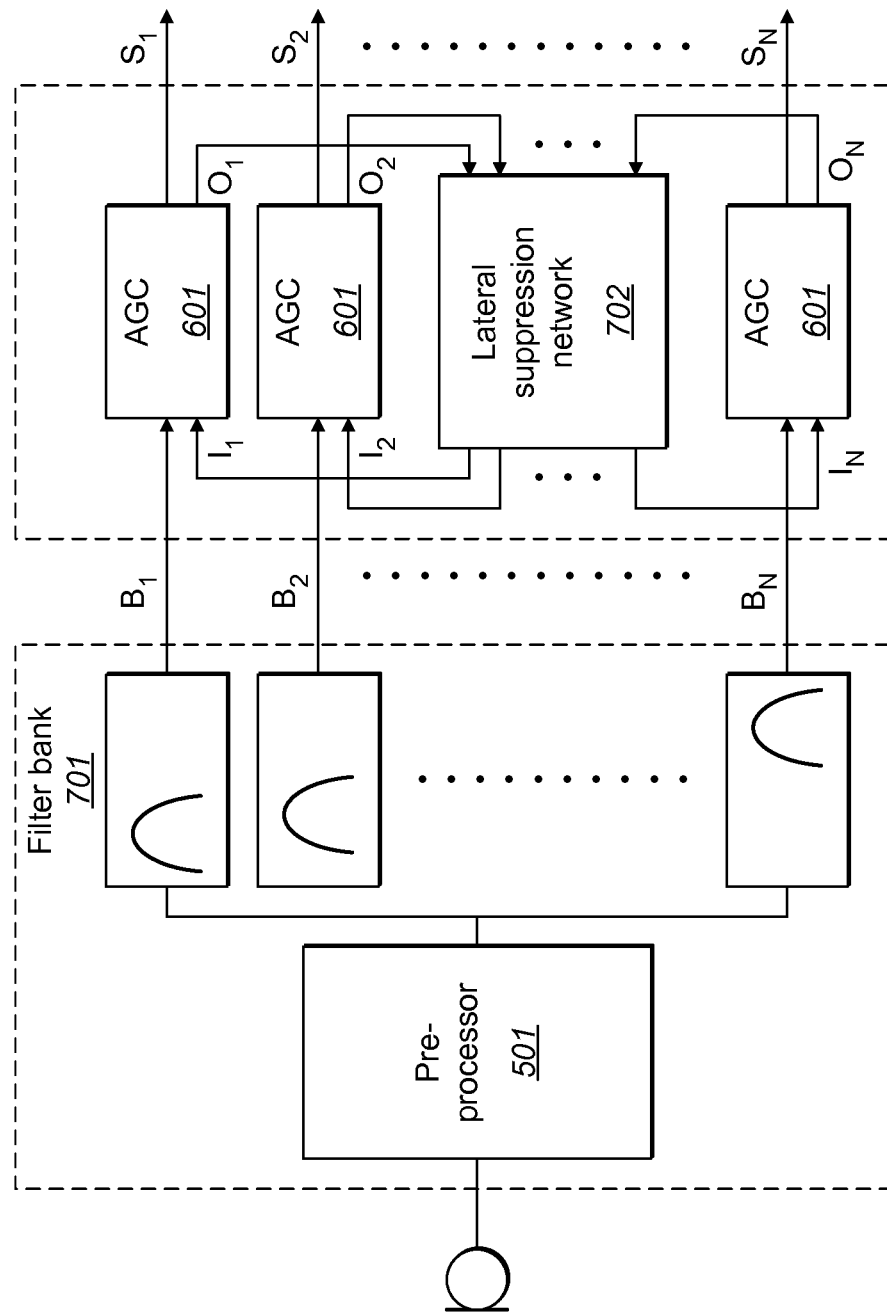
FIG. 7 shows further details of a channel specific volume control arrangement with a lateral suppression network.
Figure 8:
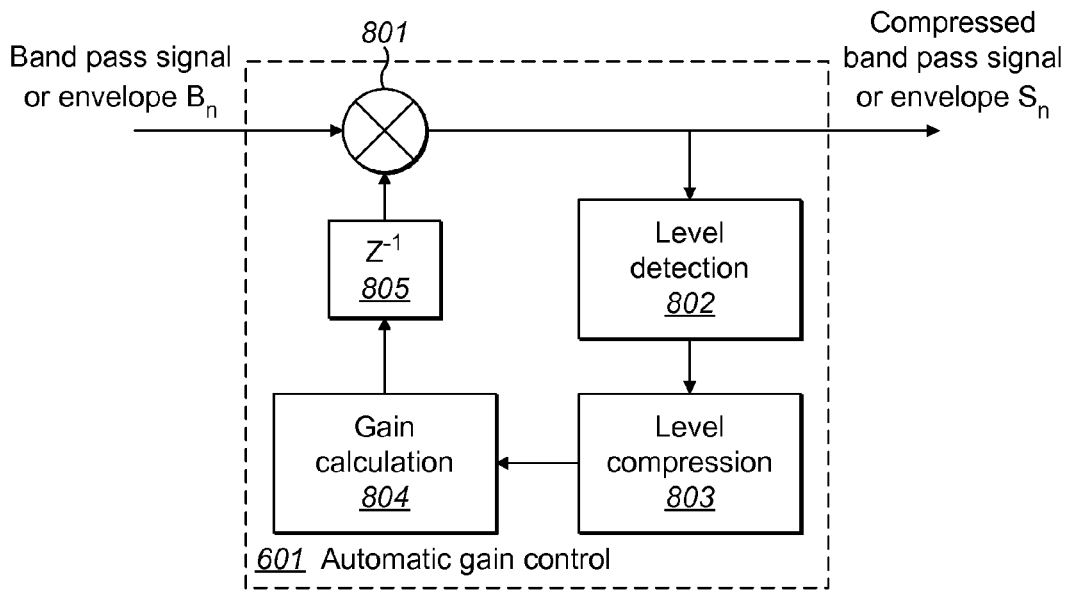
FIG. 8 shows functional details of an AGC arrangement.
Figure 9:
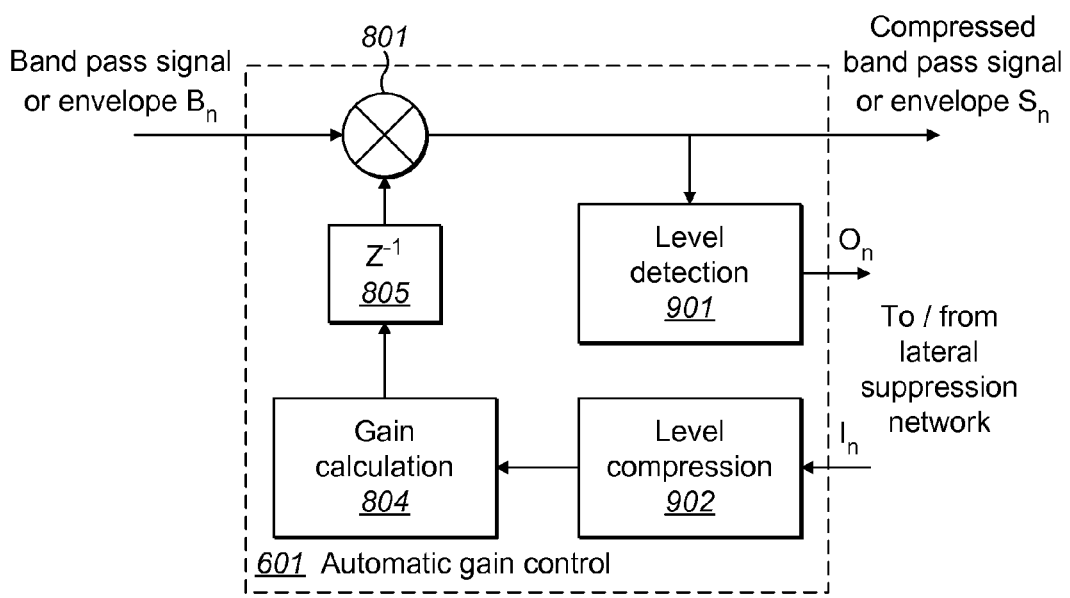
FIG. 9 shows details of an AGC arrangement with lateral suppression.

FIG. 7 shows details of the additional signal processing block including the filter bank 701 and the coupling of the AGC modules 601 with a lateral suppression network 702. FIG. 8 shows an example a typical implementation of an AGC module 601 with a signal multiplication node 801 and four main components: a level detector 802, a level compressor 803, a gain calculator 804, and delay module 804. Such AGC modules 601 are typically used in front end compression and could generally also be used for channel specific compression, but the existing structure does not allow for lateral suppression and spectral enhancement. FIG. 9 shows an improved arrangement of the AGC module 601 where the signals $O_n$ from the level detector 901 of all AGCs are routed to a lateral suppression network and the level compressor 902 of each AGC is fed by the output/return signal $I_n$ of the lateral suppression network.

In a specific embodiment, the lateral suppression network 702 could simply apply a matrix multiplication as given in Equation 1:

$$\vec{I} = W \cdot \vec{O} \qquad \text{Equation 1}$$

where W is the matrix, and I and R the vectors containing all level detector and return signals, respectively. The unit matrix (Equation 2) results in individually acting AGCs:

$$W = \begin{pmatrix} 1 & 0 & 0 & \ldots & \ldots & 0 & 0 & 0 \\ 0 & 1 & 0 & \ldots & \ldots & 0 & 0 & 0 \\ 0 & 0 & 1 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0 & 1 & 0 \\ 0 & 0 & 0 & \ldots & \ldots & 0 & 0 & 1 \end{pmatrix} \qquad \text{Equation 2}$$

whereas Equation 3 shows a setup of the lateral suppression network 702, where level detector signals of three neighboring channels are averaged:

$$W = \begin{pmatrix} 0.33 & 0.66 & 0 & \ldots & \ldots & 0 & 0 & 0 \\ 0.33 & 0.33 & 0.33 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.33 & 0.33 & 0.33 \\ 0 & 0 & 0 & \ldots & \ldots & 0 & 0.66 & 0.33 \end{pmatrix} \qquad \text{Equation 3}$$

A similar case with a subtle difference is shown in Equation 4 where elements in the main diagonal of the matrix are smaller:

$$W = \begin{pmatrix} 0.1 & 0.9 & 0 & \ldots & \ldots & 0 & 0 & 0 \\ 0.45 & 0.1 & 0.45 & \ldots & \ldots & 0 & 0 & 0 \\ 0 & 0.45 & 0.1 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.45 & 0.1 & 0.45 \\ 0 & 0 & 0 & \ldots & \ldots & 0 & 0.9 & 0.1 \end{pmatrix} \qquad \text{Equation 4}$$

In this case a channel containing smaller amplitude would be suppressed by a neighboring channel with higher amplitude. The main diagonal is set to zero in Equation 5:

$$W = \begin{pmatrix} 0 & 0.5 & 0.25 & \ldots & \ldots & 0.01 & 0 & 0 \\ 0.33 & 0 & 0.33 & \ldots & \ldots & 0.01 & 0.01 & 0 \\ 0.14 & 0.29 & 0 & \ldots & \ldots & 0.02 & 0.01 & 0 \\ \ldots & \ldots & \ldots & \ldots & \ldots & \ldots & \ldots & \ldots \\ 0 & 0.01 & 0.01 & \ldots & \ldots & 0.33 & 0 & 0.33 \\ 0 & 0 & 0.01 & \ldots & \ldots & 0.25 & 0.5 & 0 \end{pmatrix} \quad \text{Equation 5}$$

Additionally, all other elements decay exponentially. Decay characteristics can be different in the upper and lower triangular matrix. The system allows individual adjustment of the range and form of suppression in terms of analysis bands. Numerical stability of the system can be provided by normalization of the matrix and application-specific constraints.

Laterally suppressed AGCs (as described above) allow simulation of spectral masking and/or spectral sharpening effects as known from normal hearing. At the same time, distant channels can be configured to work independently. Thus, the negative side effects (described in the Background) of single channel AGC and simple independent channel specific AGCs can be avoided. For example, a low frequency signal (e.g. speech) will no longer be suppressed by a louder high frequency signal (e.g., noise). And bilaterally implanted users would be able to more correctly identify directions of simultaneous spectrally separated signals. Spectral smearing as seen with entirely independent AGCs can be avoided and spectral differences can be enhanced for further signal processing stages. Besides laterally suppressed AGCs as described above, a weighting matrix can be used with a similar architecture to implement independent AGCs or laterally averaged AGCs.

As recognized above, lateral suppression networks may be especially useful in bilateral systems where there is an implanted electrode array in both the left and right ears. As explained above, the embodiment shown in FIG. 9 uses a lateral suppression network to perform channel specific dynamic amplitude mapping of the set of band pass signals $B_n$ to generate a set of compressed band pass signals $S_n$. In specific arrangements, the band pass signals $B_n$ may be envelope or band pass signals and the compressed band pass signals 5, may be envelope signals.

The band pass signals $B_n$ are input to the AGC multiplier node 801 which is coupled to the lateral suppression network using one or more of a delay block ($Z^{-1}$) 805, a gain calculation block 804, a level compressor 902 and/or a level detector 901. The delay block 805 may delay the lateral suppression signal by one or more samples so as to form a control circuit, and/or the delay block 805 may downsample the lateral suppression signal output from the gain calculation block 804 which may also reflect an inverting functionality. The level compressor 902 may specifically perform any non-linear mapping, for example, using a non-linear MAP-law such as:

$$\log(1+C \cdot l_n)/\log(1+C) \quad \text{Equation 6}$$

The level compressor 902 multiplies the $l_n$ signal from the lateral suppression network 702 by an individual gain-constant C, increases by one, logarithmizes and scales. The gain constant C may be the same for all channels or different for each channel. In another embodiment the gain calculation block 804 may additionally down-sample the signal. Level detector 901 upsamples the compressed band pass signals $S_n$ before they are input to the lateral suppression network 702 as outgoing signals $O_n$ that suppress short harsh acoustic signals. The level detector 901 also may calculate the loudness level of the compressed band pass signals $S_n$. Due to the non-linear functions, it is necessary to up-sample the compressed band pass signals $S_n$ and run the calculations of the lateral suppression network 702 at a higher rate than the band pass signals themselves. Before multiplication by the AGC multiplication node 801, the delay block 805 downsamples the signals again.

The lateral suppression network 702 may be a multiplication matrix that reflects channel specific interaural level differences. Specifically, such a multiplication matrix may include the pre-processed signals $O_n$ from the contralateral (opposite) side of the bilateral CI system. Herein is described the use of a dynamically updated multiplication matrix, but some embodiments may be based on a static multiplication matrix with matrix coefficients that are set during a patient fitting session. The pre-processed signals $O_n$ are calculated in the same manner on both sides of the bilateral system and exchanged between the cochlear implant systems. Either directly or via a communication unit. It may be advantageous if the pre-processed signals $O_n$ are communicated in only one direction at a time from one side to the other of the bilateral CI system (e.g., based on the pre-processed signals $O_n$) though the direction of communication may alternate. The pre-processed signals $O_n$ may be averaged, for example, by means of a low-pass filter and communicated only in the case where the difference from the previously communicated pre-processed signals $O_n$ exceeds a pre-determined threshold so that the amount of data to be exchanged and the power consumption can be minimized. Such a communication threshold may depend on the listening scenario, e.g., in case of a loud environment and in case of a quiet environment.

The lateral suppression network 702 multiplication matrix W may be extended by the channels from the contra-lateral side. For example, L1 . . . L4 represents four channels from the left side cochlear implant system and R1 . . . R4 from the right side cochlear implant system. The new bilateral matrix $W_{bi}$ may be expressed by $$W_{bi}\begin{pmatrix} W_L & W_{L-R} \\ W_{R-L} & W_R \end{pmatrix} \quad \text{Equation 7}$$

Where $W_L$ and $W_R$ are the sub-matrices for the left and right sided cochlear implant systems respectively. Both sub-matrices are defined in the same way as matrix W of Equation 1. The $W_{L-R}$ and $W_{R-L}$ sub-matrices are the coupling matrices for the left sided cochlear implant system from the contralateral right sided system and vice-versa respectively, for example:

$$W_{bi} = \begin{pmatrix} 0.5 & 0.25 & 0 & 0 & 0 & 0 & 0 & 0 \\ 0.25 & 0.5 & 0.25 & 0 & 0 & 0 & 0 & 0 \\ 0 & 0.25 & 0.5 & 0.25 & 0 & 0 & 0 & 0 \\ 0 & 0 & 0.25 & 0.5 & 0 & 0 & 0 & 0 \\ 0 & 0 & 0 & 0 & 0.5 & 0.25 & 0 & 0 \\ 0 & 0 & 0 & 0 & 0.25 & 0.5 & 0.25 & 0 \\ 0 & 0 & 0 & 0 & 0 & 0.25 & 0.5 & 0.25 \\ 0 & 0 & 0 & 0 & 0 & 0 & 0.25 & 0.5 \end{pmatrix} \quad \text{Equation 8}$$

In the example shown in Equation 8, the left and right side CI systems do not distribute their level/energy from the contralateral side and the upper right and lower left 4×4 sub-matrices of the matrix are zero. In this case, the bilateral matrix $W_{bi}$ will map in the exact same way as matrix W does (Equ. 1 of application).

The example of the bilateral matrix $W_{bi}$ shown in Equation 9 does couple the left and right side CI systems:

$$W_{bi} = \begin{pmatrix} 1 & 0 & 0 & 0 & 0.2 & 0 & 0 & 0 \\ 0 & 1 & 0 & 0 & 0 & 0.2 & 0 & 0 \\ 0 & 0 & 1 & 0 & 0 & 0 & 0.2 & 0 \\ 0 & 0 & 0 & 1 & 0 & 0 & 0 & 0.2 \\ 0.2 & 0 & 0 & 0 & 1 & 0 & 0 & 0 \\ 0 & 0.2 & 0 & 0 & 0 & 1 & 0 & 0 \\ 0 & 0 & 0.2 & 0 & 0 & 0 & 1 & 0 \\ 0 & 0 & 0 & 0.2 & 0 & 0 & 0 & 1 \end{pmatrix} \quad \text{Equation 9}$$

The upper right and lower left 4×4 sub-matrices have non-zero coefficients. In Equation 9, the left and right side CI systems are coupled, but there is no lateral suppression from adjacent channels. For example channel L2 suppresses channel R1.

The bilateral matrix $W_{bi}$ shown in Equation 10 does have both coupling of the left and right side CI systems and lateral suppression from adjacent channels:

$$W_{bi} = \begin{pmatrix} 0.5 & 0.25 & 0 & 0 & 0.2 & 0 & 0 & 0 \\ 0.25 & 0.5 & 0.25 & 0 & 0.2 & 0 & 0 & 0 \\ 0 & 0.25 & 0.5 & 0.25 & 0 & 0.2 & 0 & 0 \\ 0 & 0 & 0.25 & 0.;5 & 0 & 0 & 0.2 & 0 \\ 0.2 & 0 & 0 & 0 & 0.5 & 0.25 & 0 & 0 \\ 0.2 & 0 & 0 & 0 & 0.25 & 0.5 & 0.25 & 0 \\ 0 & 0.2 & 0 & 0 & 0 & 0.25 & 0.5 & 0.25 \\ 0 & 0 & 0.2 & 0 & 0 & 0 & 0.25 & 0.5 \end{pmatrix} \quad \text{Equation 10}$$

Embodiments of the invention may be implemented in whole or in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A system for generating electrode stimulation signals for a plurality of stimulation electrodes in an implanted electrode array on a given side of a bilateral cochlear implant system having an implanted electrode array in each ear of an implanted patient, the system comprising:
a pre-processor module configured for processing an acoustic audio signal with a bank of filters to generate a set of band pass signals, each band pass signal corresponding to a band of audio frequencies associated with one of the filters;
an automatic gain control (AGC) circuit configured for performing a channel specific dynamic amplitude mapping of the band pass signals to generate a set of compressed band pass signals, the AGC circuit using a bilateral multiplication matrix characterizing a lateral suppression network and having at least one non-zero coupling element from a contralateral side;
a stimulation timing module configured for extracting stimulation information from the compressed band pass signals to generate a set of stimulation timing signals; and
a pulse shaper module configured for developing the stimulation timing signals into a set of electrode stimulation signals to the stimulation electrodes.

2. The system according to claim 1, wherein the AGC circuit includes a delay circuit that delays the amplitude mapping of the band pass signals by one or more samples.

3. The system according to claim 2, wherein the delay circuit downsamples the multiplication matrix.

4. The system according to claim 1, wherein the AGC circuit includes a gain calculation circuit that applies an individual gain constant.

5. The system according to claim 4, wherein the gain constant is the same for all band pass signals.

6. The system according to claim 4, wherein the gain constant is different for different band pass signals.

7. The system according to claim 4, wherein the gain calculation circuit includes an inverting functionality.

8. The system according to claim 1, wherein the AGC circuit includes a level compressor that performs a non-linear mapping of the lateral suppression network.

9. The system according to claim 8, wherein the non-linear mapping reflects a non-linear MAP-law.

10. The system according to claim 1, wherein the lateral suppression network includes interaural level differences.

11. A method of generating electrode stimulation signals for a plurality of stimulation electrodes in an implanted electrode array on a given side of a bilateral cochlear implant system having an implanted electrode array in each ear of an implanted patient, the method comprising:

for the stimulation electrodes of the implanted electrode array on the given side:
  i. processing an acoustic audio signal with a bank of filters to generate a set of band pass signals, each band pass signal corresponding to a band of audio frequencies associated with one of the filters;
  ii. performing a channel specific dynamic amplitude mapping of the band pass signals to generate a set of compressed band pass signals using a bilateral multiplication matrix characterizing a lateral suppression network and having at least one non-zero coupling element from a contralateral side;
  iii. extracting stimulation information from the compressed band pass signals to generate a set of stimulation timing signals; and
  iv. developing the stimulation timing signals into a set of electrode stimulation signals to the stimulation electrodes.

12. The method according to claim 11, wherein the performing the channel specific dynamic amplitude mapping includes delaying the amplitude mapping of the band pass signals by one or more samples.

13. The method according to claim 12, wherein the delaying includes downsampling the multiplication matrix.

14. The method according to claim 11, wherein an individual gain constant is applied to the multiplication matrix.

15. The method according to claim 14, wherein the gain constant is the same for all band pass signals.

16. The method according to claim 14, wherein the gain constant is different for different band pass signals.

17. The method according to claim 14, wherein an inverting functionality is applied with the gain constant.

18. The method according to claim 11, wherein the multiplication matrix reflects a non-linear mapping of the lateral suppression network.

19. The method according to claim 18, wherein the non-linear mapping includes a non-linear MAP-law.

20. The method according to claim 11, wherein the lateral suppression network includes interaural level differences.

* * * * *